United States Patent
Koch et al.

(10) Patent No.: US 7,205,349 B2
(45) Date of Patent: Apr. 17, 2007

(54) ISODECYL BENZOATE MIXTURES, PREPARATION, AND THEIR USE

(75) Inventors: Jürgen Koch, Haltern am See (DE); Michael Grass, Haltern am See (DE)

(73) Assignee: Oxeno Olefinchemie GmbH, Marl (DE)

( * ) Notice: Subject to any disclaimer, the term of this patent is extended or adjusted under 35 U.S.C. 154(b) by 79 days.

(21) Appl. No.: 10/692,753

(22) Filed: Oct. 27, 2003

(65) Prior Publication Data

US 2004/0138358 A1   Jul. 15, 2004

(30) Foreign Application Priority Data

Oct. 26, 2002   (DE) ................ 102 49 912

(51) Int. Cl.
*C08K 5/101*   (2006.01)
(52) U.S. Cl. ...................... 524/284; 526/344
(58) Field of Classification Search ............. 524/284; 526/344
See application file for complete search history.

(56) References Cited

U.S. PATENT DOCUMENTS

| | | | |
|---|---|---|---|
| 4,968,849 A | 11/1990 | Lueken et al. | |
| 5,093,534 A | 3/1992 | Ludwig et al. | |
| 5,236,987 A * | 8/1993 | Arendt | 524/287 |
| 5,268,514 A | 12/1993 | Bahrmann et al. | |
| 5,463,147 A | 10/1995 | Bahrmann et al. | |
| 6,340,778 B1 | 1/2002 | Bueschken et al. | |
| 2004/0138358 A1 | 7/2004 | Koch et al. | |
| 2005/0049341 A1 | 3/2005 | Grass et al. | |

FOREIGN PATENT DOCUMENTS

| | | | |
|---|---|---|---|
| DE | 1 962 500 | | 7/1970 |
| DE | 196 17 178 | | 11/1996 |
| DE | 199 57 522 | | 5/2001 |
| EP | 0 094 456 | | 11/1983 |
| EP | 0 326 674 | | 8/1989 |
| EP | 0 470 344 | | 2/1992 |
| EP | 0 562 451 | | 9/1993 |
| WO | WO 89/00173 | * | 1/1989 |
| WO | WO 93/20034 | | 10/1993 |
| WO | WO 97/39060 | * | 10/1997 |

OTHER PUBLICATIONS

U.S. Appl. No. 10/418,103, filed Apr. 18, 2003, Grass, et al.
U.S. Appl. No. 10/692,753, filed Oct. 27, 2003, Koch, et al.
U.S. Appl. No. 10/570,199, filed Mar. 2, 2006, Grass, et al.
U.S. Appl. No. 10/575,100, filed Apr. 10, 2006, Grass, et al.
U.S. Appl. No. 10/692,753, filed Oct. 27, 2003, Koch, et al.

* cited by examiner

*Primary Examiner*—Robert D. Harlan
(74) *Attorney, Agent, or Firm*—Oblon, Spivak, McClelland, Maier & Neustadt, P.C.

(57) ABSTRACT

The invention relates to isomeric nonyl benzoates, processes for their preparation, mixtures of the same with alkyl phthalate, alkyl adipate, or alkyl cyclohexanedicarboxylate, and also to the use of these mixtures.

12 Claims, 1 Drawing Sheet

O.Z. 6004
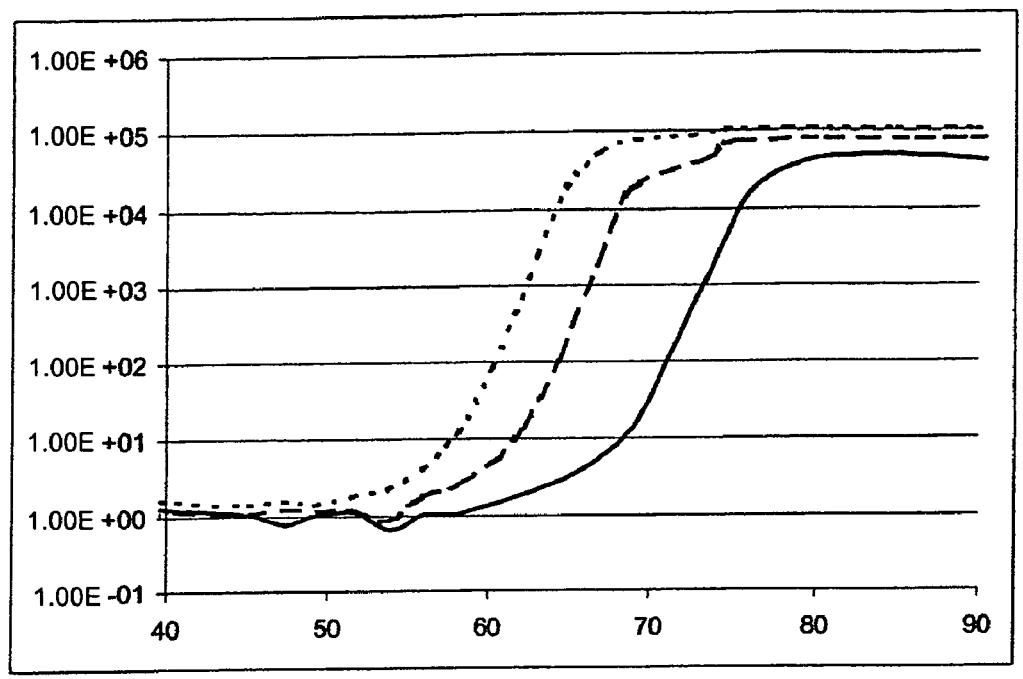
Fig 1: Gelling curves of plastisols 1-3

ISODECYL BENZOATE MIXTURES, PREPARATION, AND THEIR USE

BACKGROUND OF THE INVENTION

1. Field of the Invention

The invention relates to benzoic esters of 2-propylheptanol, of 2-propyl-4-methylhexanol, of 2-propyl-5-methylhexanol, of 2-isopropyl-4-methyl-hexanol and/or of 2-isopropyl-5-methylhexanol, to mixtures of these with alkyl phthalates, with alkyl adipates, or with alkyl cyclohexanedicarboxylates, and also to the use of these mixtures.

2. Discussion of the Related Art

Polyvinyl chloride (PVC) is one of the most important industrial polymers. It is used in a wide variety of applications, in the form of either unplasticized PVC or plasticized PVC.

To produce a plasticized PVC, plasticizers are added to the PVC, and phthalates are used in the majority of cases, in particular di-2-ethylhexyl phthalate (DEHP), diisononyl phthalate (DINP), or diisodecyl phthalate (DIDP). As the chain length of the esters increases, the solution or gelling temperatures rise, and therefore the processing temperatures of the plasticized PVC rise. The processing temperatures can be reduced again by adding what are known as fast-gellers, such as the short-chain phthalates dibutyl phthalate (DBP), diisobutyl phthalate (DIBP), benzylbutyl phthalate (BBP), or diisoheptyl phthalate (DIHP). In addition to the short-chain phthalates, dibenzoates, such as dipropylene glycol dibenzoates or the like, may also be used for the same purposes.

A property frequently exhibited by these fast-gellers in PVC plastisols, owing to their high solvating power, consists in causing a marked rise in viscosity with time. In many cases this rise in viscosity must be compensated by adding viscosity-reducers.

When PVC plastisols are prepared, the general requirement is low viscosity and minimum gelling temperature. In addition to these, a high storage stability is desirable, i.e., a low rise in viscosity of the plastisol with time.

A high viscosity is burdensome on the machinery during processing of the plastisol. Excessively high gelling temperatures reduce the production rate.

Currently, there is little knowledge of plasticizers which significantly lower the gelling temperature in a formulation and also retain a low level of viscosity of the plastisol even after storage for a number of days. 2-Ethylhexyl benzoate was recently proposed as a product which could fulfill these requirements (Bohnert, Stanhope, J. Vinyl Addit, Technol. (2000), 6(3), 146–149). However, this compound has a comparatively high vapor pressure, which often leads to unacceptable losses during processing.

DE 19 62 500 discloses the use of a mixture of relatively long-chain esters of benzoic and phthalic acid for preparing plastisols. 3,5,5-Trimethylhexanol is preferably used to prepare the benzoic esters. No precise information is given concerning the phthalic diesters to be used. U.S. Pat. No. 5,236,987 discloses the use of benzoic esters of isodecanols which have exclusively methyl branching as plasticizers or gelling agents for PVC.

The use of alkyl benzoates whose alkyl group has from 11 to 14 carbon atoms is disclosed in WO 97/39060. Although relatively long-chain esters have low volatility, they have poorer gelling properties.

In PVC, the abovementioned plasticizer systems are not completely satisfactory, and there is room for improvement not only in their volatility but also in their gelling properties, in low-temperature flexibility, and in storage stability. When preparing plasticized PVC, gelling capability has to be good and the volatility of the plasticizer has to be low. This is affected by the interactions between plasticizer and PVC polymer chain, and even slight structural changes in the molecular structure of the plasticizer molecule can therefore bring about large changes in performance characteristics.

SUMMARY OF THE INVENTION

An object of the present invention is to find new plasticizers for plastics, e.g. for PVC, which are based on low-cost raw materials and have equivalent or improved plasticizer properties, such as improved low-temperature-flexibilizing capability, while the corresponding plastisols have low viscosity.

One embodiment of the present invention provides a mixture of isomeric decyl benzoates, which includes
from 50 to 99% of 2-propylheptyl benzoate and
from 1 to 50% of at least one selected from the group including 2-isopropyl-4-methylhexyl benzoate, 2-isopropyl-5-methylhexyl benzoate, 2-propyl-4-methylhexyl benzoate, 2-propyl-5-methylhexyl benzoate, and mixtures thereof.

Another embodiment of the present invention provides a process for preparing the above mixture, which includes
esterifying, with benzoic acid,
2-propylheptanol, and
at least one selected from the group including 2-isopropyl-4-methylhexanol, 2-isopropyl-5-methylhexanol, 2-propyl-4-methylhexanol, 2-propyl-5-methylhexanol, and mixtures thereof.

Another embodiment of the present invention provides a process for preparing the above mixture, by trans-esterifying at least one selected from the group including methyl benzoate, ethyl benzoate, propyl benzoate, butyl benzoate, and mixtures thereof,
with 2-propylheptanol and at least one selected from the group including 2-isopropyl-4-methylhexanol, 2-isopropyl-5-methylhexanol, 2-propyl-4-methylhexanol, 2-propyl-5-methythexanol, and mixtures thereof.

Another embodiment of the present invention provides a polymer, plastic, PVC, or PVC plastisol, which includes the above mixture as a plasticizer.

Another embodiment of the present invention provides a paint, ink or coating material, which includes the above mixture.

Another embodiment of the present invention provides an adhesive, component thereof, or sealing compound, which includes the above mixture.

Another embodiment of the present invention relates to a composition, which includes from 5 to 90% by weight of the above-identified mixture and from 10 to 95% by weight of one or more di-$C_4$–$C_{13}$-alkyl phthalates.

Another embodiment of the present invention relates to a composition, which includes from 5 to 90% by weight of the above-identified mixture and from 10 to 95% by weight of one or more di-$C_4$–$C_{13}$-alkyl adipates.

Another embodiment of the present invention relates to a composition, which includes from 5 to 90% by weight of the above-identified mixture and from 10 to 95% by weight of one or more $C_4$–$C_{13}$ alkyl cyclohexanedicarboxylates.

DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein FIG. 1 shows a plot of that section of the viscosity/temperature curve ("gelling curve") relevant for the onset of gelling. The Y axis shows the complex viscosities in Pa·s, and the X axis shows the temperatures in ° C.

DESCRIPTION OF THE PREFERRED EMBODIMENTS

A more complete appreciation of the invention and many of the attendant advantages thereof will be readily obtained as the same becomes better understood by reference to the following detailed description.

Surprisingly, it has been found that benzoic esters of 2-propylheptanol, of 2-propyl-4-methylhexanol, of 2-propyl-5-methylhexanol, of 2-isopropyl-4-methylhexanol, and/or of 2-isopropyl-5-methylhexanol have the desired performance profile, either on their own or in a mixture with phthalic esters, and/or with dialkyl adipates, and/or with cyclohexyldicarboxylic esters. It has been found here that the performance characteristics of the ester mixture can be improved successively as the content of 2-propylheptyl benzoate increases. Without wishing to be bound by theory, the performance characteristics may be attributable to the smaller number of branches in the ester groups when comparison is made with U.S. Pat. No. 5,236,987 (generally two or more methyl branches per alkyl group).

A simple industrial method of obtaining the benzoates of the invention is aldol condensation of the C5 aldehydes n-valeraldehyde (=n-pentanal), isovaleraldehyde (2-methylbutanal), and 3-methylbutanal, followed by elimination of water, hydrogenation, and esterification using benzoic acid.

n- or isovaleraldehyde may in turn be prepared, for example, by hydroformylating 1-butene. This reaction produces varying ratios of n- and isovaleraldehyde. If this type of mixture is subjected to aldol condensation, various substituted products are obtained. Subsequent esterification using benzoic acid does not change these isomer ratios. 3-Methylbutanal is accessible via hydroformylation of isobutene.

The synthesis of the isodecanols can take place via the following steps:

a) a $C_4$ olefin or a C4 olefin mixture is hydroformylated to give the corresponding C5 aldehydes b) the aldehydes obtained in a) are aldol-condensed to give decenals c) the decenals obtained in step b) are hydrogenated to give decanols.

The starting materials used for preparing the decanol mixtures comprise 1-butene, 2-butene, isobutene, or mixtures of these olefins. Various processes can be used to hydroformylate these mixtures.

The synthesis of the isodecyl alcohols from a $C_4$ olefin or a $C_4$ olefin mixture is generally more cost-effective than the conventional route via the trimerization of propylene followed by hydroformylation and hydrogenation, a route which mainly produces methyl-branched isodecanol mixtures.

The hydroformylation generally uses unmodified or modified cobalt or rhodium catalysts.

The hydroformylation of isobutene to give 3-methylbutanal is described by way of example in the following references: V. Y. Gankin, L. S. Genender, D. M. Rudkovskii, USSR Zh. Prikl. Khim. (Leningrad) (1968), 41 (10), pp. 2275–81, incorporated by reference.

The hydroformylation of linear butenes or mixtures of these is disclosed by way of example in the publications EP 0 094 456, DE 196 17 178, EP 0 562 451 or EP 0 646 563, each incorporated herein by reference.

The usual method for the aldol condensation of n-valeraldehyde, isovaleraldehyde, 3-methylbutanal, or a mixture of $C_5$ aldehydes involves the action of basic catalysts. The catalysts used comprise alkali metal carbonates or alkali metal hydroxides, in particular compounds of sodium or of potassium, or amines, preferably tertiary amines, such as triethylamine, tri-n-propylamine, tri-n-butylamine. Combinations are possible. Operations are carried out at temperatures of from 60 to 160° C., in particular from 80 to 130° C., and at atmospheric pressure or at an elevated pressure of up to about 1 MPa. The reaction time is from a few minutes to two or more hours, and is particularly dependent on catalyst type and reaction temperature.

Each of the aforementioned ranges includes all values and subranges therebetween. The operation temperature range includes 60, 70, 80, 90, 100, 110, 120, 130, 140, 150 and 160° C. The operating pressure range includes 101, 325 Pa, 200,000, 300,000, 400,000, 500, 000, 600,000, 700,000, 800,000, 900,000 and 1,000,000 Pa. The reaction time range includes 0.1, 0.3, 0.5, 0.7, 0.9, 1, 1.1, 1.3, 1.5, 1.7, 1.9, 2, 2.1, 2.3, 2.5, 2.7, 2.9 and 3 hrs.

The aldol condensation of $C_5$ aldehydes in stirred reactors is described by way of example in WO 93/20034. Aldol condensations of aldehydes in tubular reactors are described by way of example in DE 199 57 522. The entire contents of each of these references is incorporated herein by reference.

The decenals obtained by aldol condensation of the $C_5$ aldehydes are hydrogenated in pure form or as a mixture. They are preferably hydrogenated in the liquid phase.

For the hydrogenation, use may be made of catalysts or catalyst systems which hydrogenate olefinic double bonds and also hydrogenate carbonyl groups. Catalyst systems particularly suitable for the hydrogenation of the $\alpha,\beta$-unsaturated aldehydes are those used in industry for hydrogenating 2-ethylhex-2-enal to give 2-ethylhexanol.

Preferred catalysts which may be used for the hydrogenation are copper/nickel catalysts, copper/chromium catalysts, copper/chromium/nickel catalysts, zinc/chromium catalysts, nickel/molybdenum catalysts. It is also possible to use combinations of two or more catalysts. The catalysts may be unsupported, or the hydrogenating substances or their precursors may have been applied to supports, such as silicon dioxide or aluminum dioxide.

Preferred catalysts on which the $\alpha,\beta$-unsaturated aldehydes are hydrogenated contain in each case from 0.3 to 15% by weight of copper and nickel, and also, as activators, from 0.05 to 3.5% by weight of chromium and advantageously from 0.01 to 1.6% by weight, preferably from 0.02 to 1.2% by weight, of an alkali metal component on a support material, preferably aluminum oxide and silicon dioxide. The amounts given are based on the catalysts prior to reduction. The alkali metal component is optional.

The form in which the catalysts are used is advantageously one in which they have low flow-resistance, e.g. granules, pellets or mouldings, such as tablets, cylinders, extrudates, or rings. They are advantageously activated, e.g. by heating in the stream of hydrogen, before they are used.

The hydrogenation, preferably a liquid-phase hydrogenation, is generally carried out under a total pressure of from 5 to 200 bar, in particular from 5 to 30 bar, very particularly from 15 to 25 bar, which range include 5, 10, 15, 20, 25, 30, 35, 50, 70, 90, 100, 125, 150, 175 and 200 bar. It is possible to carry out a hydrogenation in the gas phase at lower pressures, using correspondingly large gas volumes. If use is made of two or more hydrogenation reactors, the total pressures in the individual reactors can be identical or different, within the specified pressure limits.

The reaction temperatures for hydrogenation in the liquid or gaseous phase are generally from 120 to 220° C., in particular from 140 to 180° C., which ranges include 120, 140, 160, 180, 200 and 220° C.

Examples of hydrogenations of this type are described in the Patent Applications EP 0 470 344 and EP 0 326 674, each incorporated herein by reference.

The hydrogenation of decenals to give decanols may optionally be carried out in two stages. Here, the example of the first stage is hydrogenation of the olefinic double bond on a palladium catalyst and an example of the second stage is hydrogenation of the carbonyl group on one of the abovementioned catalysts.

The substances substantially present in the decanol mixtures obtained from $C_4$ olefins include one or more of the following:
2-propylheptanol, 4-methyl-2-propylhexanol, 5-methyl-2-propylhexanol, 2-isopropyl-4-methylhexanol 2-isopropyl-5-methylhexanol. Each of the decanols listed is composed of at least two stereoisomers. Mixtures of these components are termed isodecyl alcohol or isodecanol below.

As mentioned above, the composition of the decanol mixtures preferably, depends on the starting material and the hydroformylation process. All of the decanol mixtures obtained in the manner described from $C_4$ olefins may be used to prepare the esters of the invention. Preferred decanol mixtures are those which are composed of from 50 to 99%, in particular from 70 to 99%, particularly preferably from 85 to 99%, by weight, in particular from 95 to 99%, of 2-propylheptanol, which ranges include 50, 60, 70, 80, 90, 95, 97, and 99%. The higher the proportion of 2-propylheptanol in the mixture, the more advantageous the properties found in the benzoic ester prepared therefrom.

The benzoate mixtures of the invention may be used as viscosity reducers and fast-gelling plasticizers and, compared with known systems, feature a very advantageous combination of low volatility, good gelling capability, good low-temperature flexibilization, and low viscosity rise in plastisols, when used for modifying plastics, such as PVC.

The benzoic esters of the invention may be prepared by esterifying benzoic acid with the corresponding alcohols or by transesterifying other, low-molecular-weight benzoic esters.

Both variants are well known to the skilled worker (e.g. "Organikum", Wiley-VCH, 21st Edition). For the transesterification use may be made of one or more alkyl benzoates, for example, preferably methyl benzoate, ethyl benzoate, propyl benzoate, isobutyl benzoate, amyl benzoate, and/or butyl benzoate.

The present invention also provides mixtures of the isodecyl benzoates of the invention with dialkyl phthalates, preferably diisononyl phthalate, or with dialkyl adipates, preferably diisononyl adipates, or with alkyl cyclohexanedicarboxylates, preferably diisononyl cyclohexanedicarboxylate, where the dialkyl esters contain from 4 to 13, preferably from 8 to 10, carbon atoms in the alkyl group deriving from the alcohol used. These carbon atom ranges include 4, 5, 6, 7, 8, 9, 10, 11, 12 and 13 carbons.

These mixtures comprise from 5 to 90% by weight, preferably from 5 to 50% by weight, particularly preferably from 10 to 40% by weight, of the isodecyl benzoate mixtures of the invention and from 10 to 95% by weight, preferably from 50 to 95% by weight, particularly preferably from 60 to 90% by weight, of the dialkyl phthalates, dialkyl adipates, alkyl cyclo-hexanedicarboxylates.

The % by weight data for the isodecyl benzoate mixtures and the other esters give 100% in total. The % by weight data for the isodecyl benzoate isomers within the isodecyl benzoate mixture correspond to the values specified.

To prepare the cyclohexyl dicarboxylic esters and/or nonyl adipates, and/or nonyl phthalates used according to the invention it is preferable to use industrial nonanol mixtures, i.e. mixtures of the isomeric alcohols, termed isononanol or isononanol mixture in the text below.

The isomer distribution of these mixtures is determined by the way in which the nonyl alcohol (isononanol) used has been prepared.

Isononanol is prepared by hydroformylating octenes, which in turn are produced in various ways. The raw material generally used for this purpose is industrial $C_4$ streams which initially comprise all of the isomeric $C_4$ olefins alongside the saturated butanes and sometimes contaminants, such as $C_3$ and $C_5$ olefins and acetylenic compounds. Oligomerization of this olefin mixture gives mainly isomeric octene mixtures alongside higher oligomers, such as $C_{12}$ and $C_{16}$ olefin mixtures.

These octene mixtures are hydroformylated to give the corresponding aldehydes, and then hydrogenated to give the alcohol.

The composition, i.e. the isomer distribution, of the industrial nonanol mixtures depends on the starting material and on the processes of oligomerization and hydroformylation. All of these mixtures may be used to prepare the esters of the invention. Preferred nonanol mixtures are those obtained by hydroformylating $C_8$ olefin mixtures obtained by oligomerizing substantially linear butenes on nickel supported catalysts (e.g. OCTOL process), in the presence of unmodified cobalt compounds or modified or unmodified rhodium compounds, and then hydrogenating the hydroformylation mixture from which catalyst has been removed. The proportion here of isobutene in the starting material, based on the total butene content, is less than 5% by weight, preferably less than 3% by weight, particularly preferably less than 1% by weight. The result of this is that the proportion of more highly-branched nonanol isomers, including that of 3,5,5-trimethylhexanol, which has proven to be relatively disadvantageous, is markedly reduced. Mixtures of the invention therefore preferably comprise below 10% by weight, preferably below 5% by weight, particularly preferably below 3% by weight, in particular below 1% by weight, of esters of 3,5,5-trimethylhexanol. These data are based on the alcohol mixtures which would result from the hydrolysis of the ester mixtures of the invention.

The alcohol mixtures here also preferably comprise alcohols having from 7 to 15 carbon atoms (according to CAS definition, incorporated herein by reference) alongside the isonyl alcohols mentioned. The $C_7$ to $C_{15}$ alcohols include those having 7, 8, 9, 10, 11, 12, 13, 14 and 15 carbons.

Mixtures of the invention-are defined by the composition of the esters mentioned, and not by the manner or sequence of preparation of the mixtures. For the purposes of the present invention, mixtures are also present if the esters mentioned are mixed in the specified ratio, simultaneously or in succession, with another substance, such as plastics (e.g. PVC).

One preferred embodiment of the present invention also provides a process for preparing a mixture of isomeric decyl benzoates, comprising from 50 to 99% of 2-propylheptyl benzoate and from 1 to 50% by weight of 2-isopropyl-4-methylhexyl benzoate and one or more selected from the group including 2-isopropyl-5-methylhexyl benzoate, 2-propyl-4-methylhexyl benzoate and 2-propyl-5-methylhexyl benzoate, which includes using benzoic acid to esterify 2-propylheptanol and one or more of 2-isopropyl-4-methylhexanol, 2-isopropyl-5-methylhexanol, 2-propyl-4-methylhexanol, 2-propyl-5-methylhexanol, and mixtures thereof.

The esterification of the benzoic acid, phthalic acid, or phthalic anhydride, and/or adipic acid, and/or cyclohexanedicarboxylic acid, or anhydrides thereof, may be carried out using an isodecanol or one of the desired alkanols, in particular an isomerically pure nonanol or an isononanol mixture, autocatalytically or catalytically, for example using Bronstedt acids or Lewis acids, to give the corresponding esters. Irrespective of the nature of catalysis selected, the result is preferably always a temperature-dependent equilibrium between the starting materials (acid and alcohol) and the products (ester and water). In order to shift the equilibrium in favor of the ester, an entrainer may be used, with the aid of which the water of reaction is removed from the mixture. Since the alcohol mixtures used for the esterification have lower boiling points than the benzoic acid and esters thereof and have a region of immiscibility with water, they are often used as an entrainer, which can be returned back to the process after removal of water.

The alcohol or isomeric alcohol mixture used to form the ester and serving simultaneously as entrainer is used in excess, preferably of from 5 to 50%, in particular from 10 to 30%, of the amount needed to form the ester. These ranges are preferably weight percents based on the total and include all values and subranges therebetween, including 5, 10, 20, 30, 40 and 50%. Esterification catalysts which may be used are acids, such as sulfuric acid, methanesulfonic acid, or p-toluenesulfonic acid, or metals or compounds of these. Preferable examples of suitable materials are tin, titanium, zirconium, which are used in the form of finely-divided metals or advantageously in the form of their salts, oxides, or soluble organic compounds. Unlike protonic acids, the metal catalysts are high-temperature catalysts which often do not achieve their full activity until temperatures above 180° C. have been reached. However, their use is preferred, since, compared with the use of protonic catalysis, their use produces fewer by-products, such as olefins from the alcohol used. Examples of metal catalysts are tin powder, stannous oxide, stannous oxalate, titanic esters, such as tetraisopropyl orthotitanate or tetrabutyl orthotitanate, and zirconium esters, such as tetrabutyl zirconate.

The catalyst concentration depends on the nature of the catalyst. In the case of the titanium compounds preferably used, it is from 0.005 to 1.0% by weight, based on the reaction mixture, in particular from 0.01 to 0.5% by weight, very particularly from 0.01 to 0.1% by weight. These ranges include 0.005, 0.01, 0.05, 0.1, 0.5, 0.7, 0.9 and 1% by weight.

When using titanium catalysts, the reaction temperatures are from 160° C. to 270° C., preferably from 180 to 250° C. The ideal temperatures depend on the starting materials, progress of the reaction, and the catalyst concentration. They may readily be determined for every individual case by trials. Higher temperatures increase the reaction rates and favor side reactions, such as elimination of water from alcohols or formation of colored by-products. For removing the water of reaction it is advantageous that the alcohol can distill off from the reaction mixture. The desired temperature or the desired temperature range may be established via the pressure in the reaction vessel. In the case of low-boiling alcohols, the reaction is therefore carried out at superatmospheric pressure, and in the case of higher-boiling alcohols it is carried out at reduced pressure. For example, in the case of the reaction of benzoic acid with a mixture of isomeric nonanols, operations are carried out in a temperature range from 170 to 250° C. in the pressure range from 1 bar to 10 mbar.

The liquid to be introduced into the reaction may be composed to some extent or entirely of alcohol obtained by work-up of the azeotropic distillate. It is also possible for the work-up to be carried out subsequently and the liquid removed to be replaced entirely or to some extent by fresh alcohol, i.e. from alcohol provided in the feed vessel.

The crude ester mixtures, which comprise not only the ester(s) but also alcohol, catalyst or its downstream products, and sometimes by-products, are worked up by processes known per se. This work-up encompasses the following steps: removal of the excess alcohol and, where appropriate, low-boilers, neutralization of the acids present, optional steam distillation, conversion of the catalyst into a residue capable of easy filtration, removal of the solids, and, where appropriate, drying. Depending on the work-up process used, the sequence of these steps may differ.

The desired ester, e.g. isononyl or isodecyl esters, or the mixture of the esters, may optionally be removed from the reaction mixture by distillation, where appropriate after neutralization of the mixture.

As an alternative, the benzoates of the invention may be obtained by transesterifying a benzoic ester with the required decanol isomer mixture. Preferred starting materials are benzoic esters whose alkyl radicals bonded to the O atom of the ester group have from 1 to 9 carbon atoms, which range includes 1, 2, 3, 4, 5, 6, 7, 8 and 9. These radicals may be aliphatic, straight-chain or branched, alicyclic, or aromatic. One or more methylene groups of these alkyl radicals may have been substituted by oxygen. It is advantageous for the alcohols on which the starting ester is based to have lower boiling points than the isodecanol mixture or decanol used. A preferred starting material is methyl benzoate.

The ester mixtures of the invention may therefore also be prepared by using 2-propylheptanol and one or more of 2-isopropyl-4-methylhexanol, 2-isopropyl-5-methylhexanol, 2-propyl-4-methylhexanol and/or 2-propyl-5-methylhexanol to transesterify methyl benzoate, ethyl benzoate, propyl benzoate and/or butyl benzoate.

The transesterification is carried out catalytically, for example using Brönstedt acids or Lewis acids, or using bases. Irrespective of which catalyst is used, the result is preferably always a temperature-dependent equilibrium between the starting materials (alkyl benzoate and isodecanol mixture) and the products (isodecyl ester mixture and liberated alcohol). In order to shift the equilibrium in favor of the isodecyl ester mixture, the alcohol produced from the starting ester is preferably distilled off from the reaction mixture.

Here again, it is preferable to use an excess of the alcohol. Transesterification catalysts which may be used are acids, such as sulfuric acid, methanesulfonic acid, or p-toluenesulfonic acid, or metals, or compounds of these. Examples of suitable materials are tin, titanium, zirconium, which are used in the form of finely-divided metals or advantageously in the form of their salts, oxides, or soluble organic compounds. Unlike protonic acids, the metal catalysts are high-temperature catalysts which often do not achieve their full activity until temperatures above 180° C. have been reached.

However, their use is preferred, since, compared with the use of protonic catalysis, their use produces fewer by-products, such as olefins from the alcohol used. Examples of metal catalysts are tin powder, stannous oxide, stannous oxalate, titanic esters, such as tetraisopropyl orthotitanate or tetrabutyl orthotitanate, and zirconium esters, such as tetrabutyl zirconate. Combinations are possible.

Use may also be made of basic catalysts, such as oxides, hydroxides, hydrogencarbonates, carbonates, or alcoholates of alkali metals or of alkaline earth metals. From this group, preference is given to the use of alcoholates, such as sodium methoxide. Alcoholates may also be prepared in situ from an alkali metal and a decanol or an isodecanol mixture.

The catalyst concentration depends on the nature of the catalyst. It is usually from 0.005 to 1.0% by weight, based on the reaction mixture, which range includes 0.005, 0.01, 0.05, 0.1, 0.5 and 1.0%.

The reaction temperatures for the transesterification are usually from 100 to 220° C. They are preferably sufficiently high to permit distillation of the alcohol produced from the starting ester, out of the reaction mixture at the prevailing pressure, preferably atmospheric pressure.

The transesterification mixtures may be worked up in the same manner as described for the esterification mixtures.

One preferred embodiment of the invention provides benzoic esters of 2-propylheptanol, of 2-propyl-4-methylhexanol, of 2-propyl-5-methylhexanol, of 2-isopropyl-4-methyl-hexanol and/or of 2-isopropyl-5-methylhexanol, to mixtures of these with alkyl phthalates, with alkyl adipates, or with alkyl cyclohexanedicarboxylates, and also to the use of these mixtures.

Another preferred embodiment of the present invention provides mixtures of isomeric decyl benzoates, which includes from 50 to 99%, preferably from 70 to 99%, particularly preferably from 85 to 99%, of 2-propylheptyl benzoate and from 1 to 50%, preferably from 1 to 30%, particularly preferably from 1 to 15%, of 2-one or more of isopropyl-4-methylhexyl benzoate, 2-isopropyl-5-methylhexyl benzoate, 2-propyl-4-methylhexyl benzoate and/or 2-propyl-5-methylhexyl benzoate.

The mixtures of the invention may be incorporated, on their own or in combination with other plasticizers, within plastics. Preferred plastics are PVC, PVB, homo- and copolymers based on ethylene, on propylene, on butadiene, on vinyl acetate, on glycidyl acrylate, on glycidyl methacrylate, on acrylates, on acrylates with, bonded to the oxygen atom of the ester group, alkyl radicals of branched or unbranched alcohols having from 1 to 10 carbon atoms, on styrene or acrylonitrile, or on homo- or copolymers of cyclic olefins. Combinations are possible.

The following plastics may be mentioned as preferable representatives of the above groups:

polyacrylates having identical or different alkyl radicals having from 4 to 10 carbon atoms, bonded to the oxygen atom of the ester group, in particular having the n-butyl, n-hexyl, n-octyl, isononyl, or 2-ethylhexyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers, and/or nitrocellulose. Combinations are possible.

PVC grades which may be preferably used are suspension, bulk, microsuspension or preferably emulsion PVC, or else mixtures of these. Besides the esters described of cyclohexanedicarboxylic acid, phthalic acid, adipic acid, and benzoic acid, and other plasticizers, other components known to the skilled worker may be added to the formulation. Examples of these are fillers, pigments, stabilizers, lubricants, blowing agents, kickers, antioxidants, biocides, etc. Combinations are possible.

The mixtures of the invention are preferably used to prepare plastisols, in particular to prepare PVC plastisols, with particularly advantageous processing properties. These plastisols may be used in numerous products, such as synthetic leather, floorcoverings, wallpapers, etc. Particularly preferred among these applications is use in cushion vinyl (CV) floorcoverings, and in particular here in the top layer, where a further improvement in stain resistance is achieved. Use of the mixtures of the invention as a constituent of a formulation can result in plastisols with low viscosity and increased storage stability, and at the same time with very good gelling and further improved low-temperature flexibilization.

Furthermore, the benzoates of the invention or the abovementioned mixtures with phthalates, with adipates and/or with cyclohexanedicarboxylates, can be used as flexibilizers in coating materials, in paints, in inks, or in adhesives, or in components of adhesives, or in sealing compounds.

EXAMPLES

Having generally described this invention, a further understanding can be obtained by reference to certain specific examples which are provided herein for purposes of illustration only and are not intended to be limiting unless otherwise specified.

Example 1

Preparation of an Isodecyl Alcohol Mixture as Starting Material for the Benzoic Esters (Invention Example)

2-Propylheptanol and 2-propyl-4-methylhexanol are prepared by a synthetic sequence known from the literature (hydroformylation of 1-butene, then aldolization of the resultant aldehydes and hydrogenation of the decenals). A ratio of 90% by weight of 2-propylheptanol and 10% by weight of 2-propyl-4-methylhexanol is established by adding pure 2-propylheptanol.

Example 2

Preparation of the Benzoate (Invention Example)

976 g of benzoic acid (8 mol), 1872 g of isodecyl alcohol mixture from example 1 (12 mol), and 0.59 g of tetra butyl titanate (0.06%, based on the amount of acid) are weighed into a 4 liter distillation flask with superimposed water separator e.g. dean-stark-trap and reflux condenser, and with a sampling neck and thermometer, and heated to boiling under nitrogen. The water of reaction produced during the esterification was regularly removed. When after about 3 hours the acid value fell below 0.1 mg KOH/g, the excess alcohol was distilled off in vacuo via a 10 cm column filled with Raschig rings. The mixture was then cooled to 80° C. and transferred to a 4 liter reaction flask with immersion tube, superimposed dropping funnel, and column, and attached to a Claisen bridge. A sodium hydroxide solution (5 weight-%) was then used for neutralization (about 10-fold excess of alkali solution). The mixture was then heated in vacuo (10 mbar) to 190° C. 8% of deionized water, based on the amount of crude ester used, was then added dropwise via the dropping funnel, at constant temperature. After addition of the water, the heating was switched off and the mixture was cooled in vacuo.

The ester was filtered at room temperature through a suction funnel with filter paper and filtration aid. Gas chromatography determined the purity of the ester as 99.9%.

Example 3

Preparation of Isodecyl Benzoate from Predominantly Methyl-Branched Isodecanol (Comparative Example)

A typical representative of a C10 alcohol mixture which has branching practically exclusively consisting of methyl groups is Exxal 10, an isodecyl alcohol mixture from ExxonMobil Chemical.

The esterification described in example 2 is repeated using Exxal 10 instead of the isodecyl alcohol mixture used in that example. The purity of the corresponding ester is 99.8%.

Example 4

Preparation of Plastisols on the Basis of the Benzoates from Examples 2 and 3

Only the two fast-gelling plasticizers are represented in formulations A and B, to accentuate the differences between these grades. Formulations C and D comprise industrially relevant mixtures of VESTINOL 9 (DINP from OXENO Olefinchemie GmbH) and fast-gellers in typical top-coat formulations.

The weight used of the components is given in the table below.

TABLE 1

| Formulations (all data in phr (=parts by weight per 100 parts of PVC)) | | | | |
|---|---|---|---|---|
|  | A | B | C | D |
| VESTOLIT B 7021 (Emulsion PVC) | 100 | 100 | 100 | 100 |
| VESTINOL 9 (DINP, OXENO) | 0 | 0 | 35 | 35 |
| Isodecyl benzoate (from example 2, according to the invention) | 50 | 0 | 15 | 0 |
| Methyl-branched isodecyl benzoate (from example 3; comparative example) | 0 | 50 | 0 | 15 |
| Drapex 39 (costabilizer, Crompton) | 3 | 3 | 3 | 3 |
| Mark CZ 140 (Ca/Zn-stab., Crompton) | 1.5 | 1.5 | 1.5 | 1.5 |

The plasticizers were temperature-controlled to 25° C. prior to addition. The liquid constituents were weighed first into a PE beaker, and then the pulverulent constituents. The mixture was manually mixed using a paste spatula until all of the powder had been wetted. The mixing beaker was then clamped into the clamping equipment of a dissolver mixer. Prior to immersing the stirrer into the mixture, the rotation rate was set to 1 800 revolutions per minute. After the stirrer had been switched on, stirring was continued until the temperature of the digital display of the temperature sensor reached 30.0° C. This ensured that homogenization of the plastisol was achieved with defined energy input. The temperature of the plastisol was then immediately controled to 25° C.

Example 5

Measurement of Viscosities of Plastisols

The viscosities of the plastisols prepared in example 4 were measured as follows by a method based on DIN 53 019, using the Physica DSR 4000 rheometer, which is controled by US 200 software, the entire contents of each of which being incorporated by reference.

The plastisol was again stirred with a spatula in the feed vessel and was tested in accordance with the operating instructions in test system Z3 (DIN 25 mm). Measurement proceeded automatically at 25° C. by way of the abovementioned software. The settings were as follows:

pre-shear of 100 $s^{-1}$ for a period of 60 s, during which no values were measured, a downward progression beginning at 200 $s^{-1}$ and ending at 0.1 $s^{-1}$, divided into a logarithmic series with 30 steps, the duration of each point of measurement being 5 s.

After the test, the test data were processed automatically by the software. The viscosity was plotted as a function of the shear rate. Each of the measurements was made after 2 h and 24 h. Between these junctures, the paste was stored at 25° C.

The two tables below list these viscosity values obtained after each of the storage times given, for shear rates of 1.06 $s^{-1}$ and 118 $s^{-1}$.

TABLE 2

| Shear rate 1.06 $s^{-1}$ (viscosity data in Pa*s) | | | | |
|---|---|---|---|---|
| Formulation | A | B | C | D |
| 2 h | 0.66 | 0.69 | 2.06 | 2.13 |
| 24 h | 0.80 | 0.82 | 2.34 | 2.40 |

TABLE 3

| Shear rate 118 $s^{-1}$ (viscosity data in Pa*s) | | | | |
|---|---|---|---|---|
| Formulation | A | B | C | D |
| 2 h | 0.64 | 0.65 | 2.79 | 2.84 |
| 24 h | 0.72 | 0.74 | 3.02 | 3.12 |

There is practically no difference between the viscosities of the plastisols to be compared: A and B and, respectively, C and D.

Example 6

Gelling Properties of Plastisols Prepared in Accordance with Example 4

The gelling performance of the plastisols was tested in a Bohlin CVO oscillation viscometer (measurement system PP20), operated with shear stress control.

The following parameters were set:
Mode: Temperature gradient
Start temperature: 25° C.
End temperature: 180° C.
Heating/cooling rate: 2° C./min
Temperature after measurement: 25° C.
Oscillation frequency: 2 Hz
Delay time: 1 s
Waiting time: 15 s
Continuous oscillation: on
Automatic shear stress preset: on
Shear stress at start: 0.3 Pa
Required deformation: 0.002
Gap width: 0.5 mm
Test procedure:

A spatula was used to apply a drop of the plastisol to be tested (formulations C and D from example 4), free from air bubbles, to the lower plate of the test system. Care was taken here that some plastisol could exude uniformly out of the measurement system (not more than about 6 mm overall) after the measurement system has been closed. The protective covering, which also serves for thermal insulation, is then superimposed, and the test is started.

The "complex viscosity" of the plastisol was plotted as a function of temperature. The start of gelling is recognizable via a sudden marked rise in complex viscosity. The earlier the onset of this viscosity rise, the better the gelling capability of the system.

FIG. 1 plots that section of the viscosity/temperature curve ("gelling curve") relevant for the onset of gelling. The Y axis shows the complex viscosities in Pa·s, and the X axis shows the temperatures in ° C. The continuous line denotes plastisol C (with isodecyl benzoate of the invention), and the dotted line denotes plastisol D (with methyl-branched isodecyl benzoate, comparative example).

It can be seen that the shapes of the two curves are practically superimposable, and it can therefore be assumed that both grades of isodecyl benzoate have comparable gelling performance.

Example 7

Determination of Glass Transition Temperature of the Two Benzoates

The addition of a plasticizer lowers the glass transition temperature of PVC sufficiently for the material to retain flexibility even at low temperatures. The capability of a plasticizer to lower the glass transition temperature TG becomes greater as the glass transition temperature of the appropriate plasticizer substance reduces.

Measuring the glass transition temperature of the pure plasticizer therefore permits conclusions to be drawn concerning its low-temperature flexibilization potential.

An example of a method for determining $T_G$ is dynamic scanning calorimetry (DSC) or torsional braid analysis (TBA). In the cases described here, the TBA method was used for reasons of greater accuracy. This is a variant of the "traditional" torsional oscillation analysis (TOA) described in DIN EN ISO 6721 Part 2, for example, incorporated herein by reference. In TBA, the material to be tested (in this case the products mentioned in examples 2 and 3) was applied (loading between 18 and 25% by weight) to a desized glass fiber roving in the form of a braid. The stiffness G' and the loss modulus G" were determined in each case at temperatures of from −180 to +100° C., at frequency 1 s$^{-1}$ in the torsion-pendulum test (MYRENNE ATM III). The glass transition temperature $T_G$ could be determined from the maximum of G'. A $T_G$ of −92° C. was determined for the isodecyl benzoate prepared according to the invention as in example 2. A $T_G$ mof −90° C. was determined for the comparative example, the isodecyl ester from example 3, whose branching consisted exclusively of methyl groups.

The accuracy of the method being from 0.5 to 1° C., this difference therefore has to be regarded as significant.

In summary, it can be said that the isodecyl benzoate of the invention differs substantially from the comparative example in terms of improved low-temperature flexibilization, expressed via the glass transition temperature $T_G$ of the plasticizer, and in terms of the more cost-effective preparation process resulting from the different raw materials used to prepare the alcohols.

Obviously, numerous modifications and variations of the present invention are possible in light of the above teachings. It is therefore to be understood that within the scope of the appended claims, the invention may be practiced otherwise than as specifically described herein.

This application is based on German Patent application DE 102 49 912.8, filed Oct. 26, 2002, the entire contents of which being herein incorporated by reference.

What is claimed is:

1. A plastic comprising a plasticizer which contains:
a mixture of isomeric decyl benzoates, comprising:
from 50 to 99% of 2-propylheptyl benzoate and
from 1 to 50% of at least one decyl benzoate selected from the group consisting of 2-isopropyl-4-methylhexyl benzoate 2-isopropyl-5-methylhexyl benzoate, 2-propyl-4-methylhexyl benzoate, 2-propyl-5-methylhexyl benzoate, and mixtures thereof.

2. The plastic of claim 1,
which is selected from the group consisting of PVC, PVB, a homopolymer and a copolymer,
wherein said homopolymer or copolymer is based on
ethylene,
propylene,
butadiene,
vinyl acetate,
glycidyl acrylate,
glycidyl methacrylate,
acrylates,
acrylates bonded to the oxygen atom of the ester group, alkyl radicals of branched or unbranched alcohols having from 1 to 10 carbon atoms,
styrene or acrylonitrile,
homo- or copolymers of cyclic olefins, and combinations thereof.

3. The plastic of claim 1,
which is selected from the group consisting of:
polyacrylate having identical or different alkyl radicals having from 4 to 10 carbon atoms bonded to the oxygen atom of the ester group,
polymethacrylate,
polymethyl methacrylate,
methyl acrylate-butyl acrylate copolymer,
methyl methacrylate-butyl methacrylate copolymer,
ethylene-vinyl acetate copolymer,
chlorinated polyethylene,
nitrile rubber,
acrylonitrile-butadiene styrene copolymer,
ethylene-propylene copolymer,
ethylene-propylene-diene copolymer,
styrene-acrylonitrile copolymer,
acrylonitrile-butadiene rubber,
styrene-butadiene elastomer, methyl methacrylate-styrene-butadiene copolymer,
nitrocellulose, and
combinations thereof.

4. A paint, ink or coating material, adhesive, or sealing compound, comprising:
a mixture of isomeric decyl benzoates, comprising:
from 50 to 99% of 2-propylheptyl benzoate and
from 1 to 50% of at least one decyl benzoate selected from the group consisting of 2-isopropyl-4-methylhexyl benzoate, 2-isopropyl-5-methylhexyl benzoate, 2-propyl-4-methylhexyl benzoate, 2-propyl-5-methylhexyl benzoate, and mixtures thereof.

5. A composition containing from 5 to 90% by weight a mixture of isomeric decyl benzoates, comprising:
from 50 to 99% of 2-propylheptyl benzoate and from 1 to 50% of at least one decyl benzoate selected from the group consisting of 2-isopropyl-4-methylhexyl benzoate, 2-isopropyl-5-methylhexyl benzoate, 2-propyl-4-methylhexyl benzoate, 2-propyl-5-methylhexyl benzoate, and mixtures thereof; and
from 10 to 95% by weight of
diisononyl adipate or one or more $C_4$–$C_{13}$ alkyl cyclohexanedicarboxylates.

6. The composition of claim 5, which contains 10 to 95% of dialkyl adipate.

7. The composition as claimed in claim 5, which contains 10 to 95% of diisononyl cyclohexanedicarboxylate.

8. A mixture of isomeric decyl benzoates, comprising:
from 50 to 99% of 2-propylheptyl benzoate and
from 1 to 50% of at least one decyl benzoate selected from the group consisting of 2-isopropyl-4-methylhexyl benzoate, 2-isopropyl-5-methylhexyl benzoate, 2-propyl-4-methylhexyl benzoate, 2-propyl-5-methylhexyl benzoate, and mixtures thereof,
further comprising of one or more di- $C_4$–$C_{13}$-alkyl adipates, or one or more $C_4$–$C_{13}$ alkyl cyclohexanedicarboxylates.

9. The mixture as claimed in claim 8, which further comprise one or more di- $C_4$–$C_{13}$-alkyl adipates.

10. The mixture as claimed in claim 8,
further comprising one or more $C_4$–$C_{13}$ alkyl cyclohexanedicarboxylates.

11. The mixture as claimed in claim 8, further comprising a $C_4$–$C_{13}$ alkyl cyclohexanedicarboxylate which is diisononyl cyclohexanedicarboxylate.

12. The mixture as claimed in claim 8,
further comprising a di- $C_4$–$C_{13}$-alkyl adipate which is diisononyl adipate.

* * * * *